(12) United States Patent
Nemoto

(10) Patent No.: US 7,844,328 B2
(45) Date of Patent: Nov. 30, 2010

(54) LIQUID INJECTOR FOR CONTROLLING INJECTION OF LIQUID IN REAL-TIME ACCORDING TO INJECTION GRAPH

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 1611 days.

(21) Appl. No.: 10/691,571

(22) Filed: Oct. 24, 2003

(65) Prior Publication Data

US 2004/0199076 A1 Oct. 7, 2004

(30) Foreign Application Priority Data

Apr. 1, 2003 (JP) .............................. 2003-098057

(51) Int. Cl.
*A61B 6/00* (2006.01)
*A61M 5/00* (2006.01)
(52) U.S. Cl. .......................... 604/21; 604/116; 600/432; 382/128; 128/922
(58) Field of Classification Search .................. 604/30, 604/246, 131, 187, 21, 116, 188; 600/431–432; 128/898, 922; 345/440.1, 440–443, 156, 345/179–180, 182–183
See application file for complete search history.

(56) References Cited

U.S. PATENT DOCUMENTS

| | | | | | |
|---|---|---|---|---|---|
| 4,177,354 | A | * | 12/1979 | Mathews .................. | 178/19.05 |
| 4,641,354 | A | * | 2/1987 | Fukunaga et al. ........... | 382/189 |
| 4,972,496 | A | * | 11/1990 | Sklarew ...................... | 382/187 |
| 5,309,171 | A | * | 5/1994 | Nakatani .................. | 345/440.1 |
| 5,365,254 | A | * | 11/1994 | Kawamoto .................. | 345/157 |
| 5,535,317 | A | * | 7/1996 | Tanaka et al. ............... | 345/440 |
| 5,631,667 | A | * | 5/1997 | Cadwell .................. | 345/440.1 |
| 5,687,208 | A | * | 11/1997 | Bae et al. ...................... | 378/8 |
| 5,757,357 | A | * | 5/1998 | Grande et al. ............ | 345/440.1 |
| 5,851,184 | A | * | 12/1998 | Goethel ...................... | 600/431 |
| 6,055,985 | A | * | 5/2000 | Bae et al. ...................... | 604/28 |
| 6,195,617 | B1 | * | 2/2001 | Miller ........................ | 702/125 |
| 6,366,683 | B1 | * | 4/2002 | Langlotz .................... | 382/128 |
| 6,603,477 | B1 | * | 8/2003 | Tittle .......................... | 345/440 |
| 6,618,041 | B2 | * | 9/2003 | Nishizawa .................. | 345/173 |
| 6,648,823 | B2 | * | 11/2003 | Thompson .................. | 600/300 |
| 6,704,012 | B1 | * | 3/2004 | Lefave ........................ | 345/440 |
| 6,734,857 | B2 | * | 5/2004 | Loughner, II ............ | 345/440.1 |

(Continued)

FOREIGN PATENT DOCUMENTS

JP 5-298046 11/1993

(Continued)

*Primary Examiner*—Nicholas D Lucchesi
*Assistant Examiner*—Quynh-Nhu H Vu
(74) *Attorney, Agent, or Firm*—Oblon, Spivak, McClelland, Maier & Neustadt, L.L.P.

(57) ABSTRACT

A liquid injector displays a plotting chart image whose vertical axis represents liquid injection rates and horizontal axis represents liquid injection times. When an injection graph which represents a liquid injection rate at each quantity of the liquid to be injected is entered into the displayed plotting chart image, the liquid injector controls operation of an injection performing means according to the injection graph and a time which has elapsed from the start of injection of the liquid. The rate at which the liquid is injected can thus be changed as desired with time according to the injection graph.

21 Claims, 16 Drawing Sheets

U.S. PATENT DOCUMENTS

| | | | |
|---|---|---|---|
| 7,013,430 B2* | 3/2006 | Jaffe | 715/771 |
| 7,203,353 B2* | 4/2007 | Klotz et al. | 382/131 |
| 7,443,396 B2* | 10/2008 | Ilic | 345/440.1 |
| 7,570,262 B2* | 8/2009 | Landau et al. | 345/440 |
| 2002/0030683 A1* | 3/2002 | Alexander | 345/440.1 |
| 2002/0107476 A1* | 8/2002 | Mann et al. | 604/67 |
| 2004/0057061 A1* | 3/2004 | Bochkarev | 358/1.9 |

FOREIGN PATENT DOCUMENTS

| | | |
|---|---|---|
| JP | 6-177 | 1/1994 |
| JP | 9-282476 | 10/1997 |
| JP | 11-347118 | 12/1999 |
| JP | 2002-11096 | 1/2002 |
| JP | 2002-102343 | 4/2002 |
| WO | WO 00/48112 | 8/2000 |

* cited by examiner

LIQUID INJECTOR FOR CONTROLLING INJECTION OF LIQUID IN REAL-TIME ACCORDING TO INJECTION GRAPH

BACKGROUND OF THE INVENTION

1. Field of the Invention

The present invention relates to a liquid injector for injecting a liquid into a subject, and more particularly to a liquid injector for injecting a liquid, such as a contrast medium, into a subject who is to be imaged by an imaging diagnostic apparatus such as a CT (Computed Tomography) apparatus, an MRI (Magnetic Resonance Imaging) apparatus, a PET (Positron Emission Tomography) apparatus, or the like.

2. Description of the Related Art

Presently available imaging diagnostic apparatus for capturing fluoroscopic images of subjects include CT scanners, MRI apparatus, PET apparatus, ultrasonic diagnostic apparatus, CT angiography apparatus, MR angiography apparatus, and ultrasonograph. When such an imaging diagnostic apparatus is used to capture a fluoroscopic image of a subject, it is occasionally practiced to inject a liquid such as a contrast medium or a saline solution into the subject. There has been put to practical use a liquid injector for automatically injecting a liquid into a subject.

Such a liquid injector has a drive motor and a slider mechanism, and employs a liquid syringe that is removably mounted. The liquid syringe comprises a cylinder and a piston slidably inserted in the cylinder. The cylinder is filled with a liquid such as a contrast medium or a saline solution to be injected into the subject.

The liquid syringe is connected to the subject by an extension tube and set on an injection performing means. The injection performing means individually holds the piston and the cylinder and moves them relatively to each other for injecting a liquid, typically a contrast medium, from the liquid syringe into the subject.

The operator determines the rate at which the contrast medium is to be injected and the total quantity of the contrast medium to be injected, in view of various conditions, and then enters numerical data representing the rate and total quantity into the liquid injector. Based on the entered numerical data, the liquid injector injects the contrast medium into the subject at the rate and in the quantity represented by the entered numerical data. The injected contrast medium changes the image contrast of the subject, allowing the imaging diagnostic apparatus to capture a good fluoroscopic image of the subject.

Some liquid injectors are capable of injecting a saline solution as well as a contrast medium into the subject. For operating such a liquid injector, the operator enters, if desired, an instruction to inject the saline solution following the completion of the injection of the contrast medium, together with data representing the rate at which the saline solution is to be injected and the total quantity of the saline solution to be injected, into the liquid injector.

Based on the entered data, the liquid injector first injects the contrast medium and then automatically injects the saline solution after the contrast medium has been injected. The subsequently injected saline solution pushes the previously injected contrast medium, reducing the consumption of the contrast medium, and also reduces artifacts in the captured image.

Liquid injectors of the type described above have been devised and applied for patent by the applicant of the present application (see, for example, patent documents 1, 2 below).

Patent document 1: Japanese laid-open patent publication No. 2002-11096;
Patent document 2: Japanese laid-open patent publication No. 2002-102343.

The above liquid injector is capable of injecting a contrast medium into the subject in order to change the image contrast of the subject to a state which allows the imaging diagnostic apparatus to capture a good fluoroscopic image of the subject.

When a contrast medium for CT was actually injected into a subject by the liquid injector and a time-dependent change in the CT value, which represents the image contrast, was measured, it was found that even if the contrast medium was injected at a constant rate, the CT value was not constant, but rose nonlinearly and then fell, and remained at an optimum level for a very short period of time.

Therefore, the conventional liquid injector which injects a contrast medium at a constant rate that is represented by entered numerical data fails to provide optimum-imaging conditions in an imaging diagnostic apparatus combined therewith. For solving the above problem, it is necessary to change, with time, the rate at which the contrast medium is injected. For example, it is known in the art to divide one cycle of liquid injection into a plurality of phases and set numerical values of a liquid injection rate and a liquid injection time for each of the phases.

However, it is a complex procedure to set and enter numerical data for liquid injection rates which are actually to be changed with time. Even when the numerical values of the liquid injection rate and the liquid injection time represented by the entered numerical data are displayed in each of the phases, it is difficult to gain an intuitive understanding of time-dependent changes of the liquid injection rates.

Unskilled operators are unable to carry out such a complex procedure and may possibly enter inappropriate numerical data. In addition, the above process of setting numerical values of a liquid injection rate and a liquid injection time for each of the plural phases fails to set nonlinearly changing liquid injection rates.

SUMMARY OF THE INVENTION

It is therefore an object of the present invention to provide a liquid injector which is capable of easily setting liquid injection rates which change with time.

A first liquid injector according to the present invention has an injection performing means, an image displaying means, a graph entering means, a graph storing means, a graph displaying means, a time measuring means, and an injection control means. The image displaying means displays a plotting chart image having a vertical axis representative of liquid injection rates and a horizontal axis representative of liquid injection times. The graph entering means accepts an input action to enter an injection graph which represents a liquid injection rate at each liquid injection time into the plotting chart image. The graph storing means stores data of the entered injection graph. The graph displaying means displays an image of the entered injection graph whose data is stored on the displayed plotting chart image. The injection control means controls operation of the injection performing means in real-time according to the measured time that has elapsed and the entered injection graph.

When an injection graph which represents a liquid injection rate at each liquid injection time is entered into the displayed plotting chart image, the first liquid injector changes the liquid injection rate with the time that has elapsed according to the injection graph. Therefore, a complex liquid injection process for injecting a liquid at a chronologically changing injection rate can be carried out through simple input actions.

In a second liquid injector according to the present invention, the image displaying means displays a plotting chart image whose vertical axis represents quantities of the liquid to be injected and the horizontal axis represents liquid injection times. The graph entering means accepts an input action to enter an injection graph which represents a quantity of the liquid to be injected at each liquid injection time into the plotting chart image. The injection control means controls operation of the injection performing means in real-time according to the measured time and the entered injection graph.

When an injection graph which represents a quantity of the liquid to be injected at each liquid injection time is entered into the displayed plotting chart image, the second liquid injector manages the quantity of the liquid to be injected with the time that has elapsed according to the injection graph. Therefore, a complex liquid injection process for injecting a liquid in a chronologically changing quantity can be carried out through simple input actions.

In a third liquid injector according to the present invention, a quantity detecting means is employed in place of the time measuring means, and the image displaying means displays a plotting chart image whose vertical axis represents liquid injection rates and horizontal axis represents quantities to be injected of the liquid. The graph entering means accepts an input action to enter an injection graph which represents a liquid injection rate at each quantity of the liquid to be injected into the plotting chart image. The quantity detecting means detects an injected quantity of the liquid from at least a start of injection of the liquid. The injection control means controls operation of the injection performing means in real-time according to the detected injected quantity and the entered injection graph. Thus, the third liquid injector changes the liquid injection rate depending on the quantity of the liquid to be injected.

When an injection graph which represents a liquid injection rate at each quantity of the liquid to be injected is entered into the displayed plotting chart image, the third liquid injector changes the liquid injection rate depending on the quantity of the liquid to be injected according to the injection graph. Thus, a complex liquid injection process for injecting a liquid at a liquid injection rate that changes depending on the quantity of the liquid to be injected can be carried out through simple input actions.

The various means referred to in the present invention may be arranged to perform their stated functions, and may be implemented by dedicated pieces of hardware for performing the functions, data processing apparatus for performing the functions according to computer programs, functions achieved in data processing apparatus according to computer programs, or combinations thereof.

The various means referred to in the present invention are not required to be individually independent entities, and may be arranged such that a plurality of means may be constructed as a single apparatus, a certain means may be part of another means, or part of a certain means and part of another means overlap each other.

A computer unit referred to in the present invention may comprise a piece of hardware capable of reading the data of a computer program and performing a processing operation according to the computer program, and may comprise a CPU (Central Processing Unit) to which are connected various devices including a ROM (Read Only Memory), a RAM (Random Access Memory), an I/F (Interface) unit, etc.

According to the present invention, enabling a computer unit to carry out various operations according to a computer program also signifies enabling the computer unit to control operation of various devices to carry out various operations. For example, storing various data in a computer unit may signify enabling a CPU to store various data in an information storage medium such as a RAM or the like fixedly mounted in the computer unit, or enabling a CPU to store various data in an information storage medium such as an FD (Flexible Disc-cartridge) or the like replaceably loaded in the computer unit through an FDD (FD Drive).

An information storage medium referred to in the present invention may comprise a piece of hardware which stores in advance a computer program for enabling a computer unit to perform various processing operations.

An information storage medium may comprise, for example, a ROM or an HDD (Hard Disc Drive) fixedly mounted in the computer unit, or a CD (Compact Disc)-ROM or an FD replaceably loaded in the computer unit.

The above and other objects, features, and advantages of the present invention will become apparent from the following description with reference to the accompanying drawings which illustrate examples of the present invention.

DETAILED DESCRIPTION OF THE PREFERRED EMBODIMENTS

Figure 4:
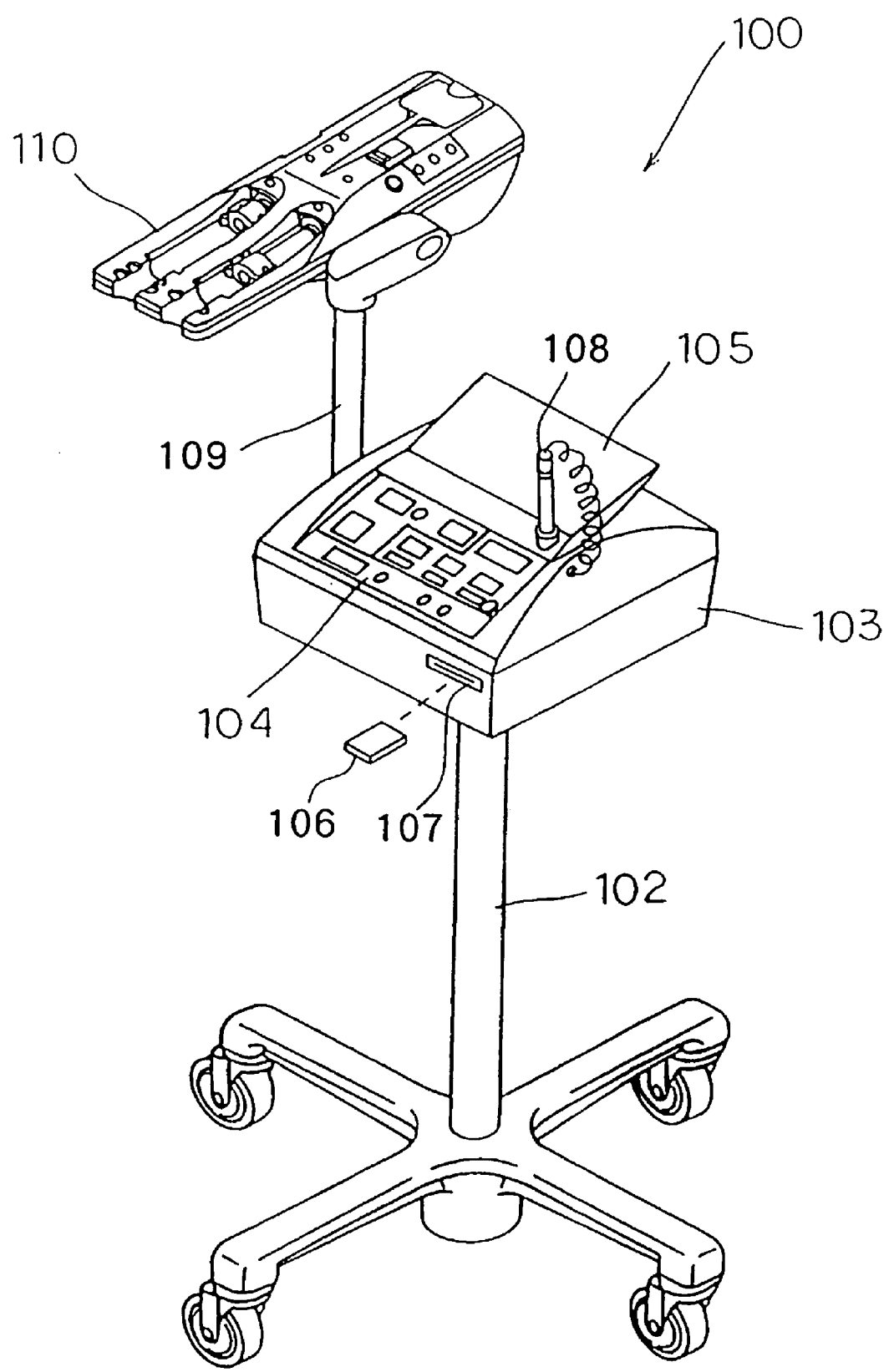
FIG. 4 is a perspective view of the liquid injector.

A liquid injector according to an embodiment of the present invention will be described below with reference to the drawings. As shown in FIG. 4, liquid injector 100 according to an embodiment of the present invention has main body 103 mounted on the upper end of stand 102. Main body 103 supports thereon console panel 104, touch panel 105, card drive 107 for PC card 106 which serves as an information storage medium, and write pen 108. Movable arm 109 is vertically mounted on a side wall of main body 103, and injection head 110 as a syringe holder is mounted on the upper end of movable arm 109.

Figure 3:
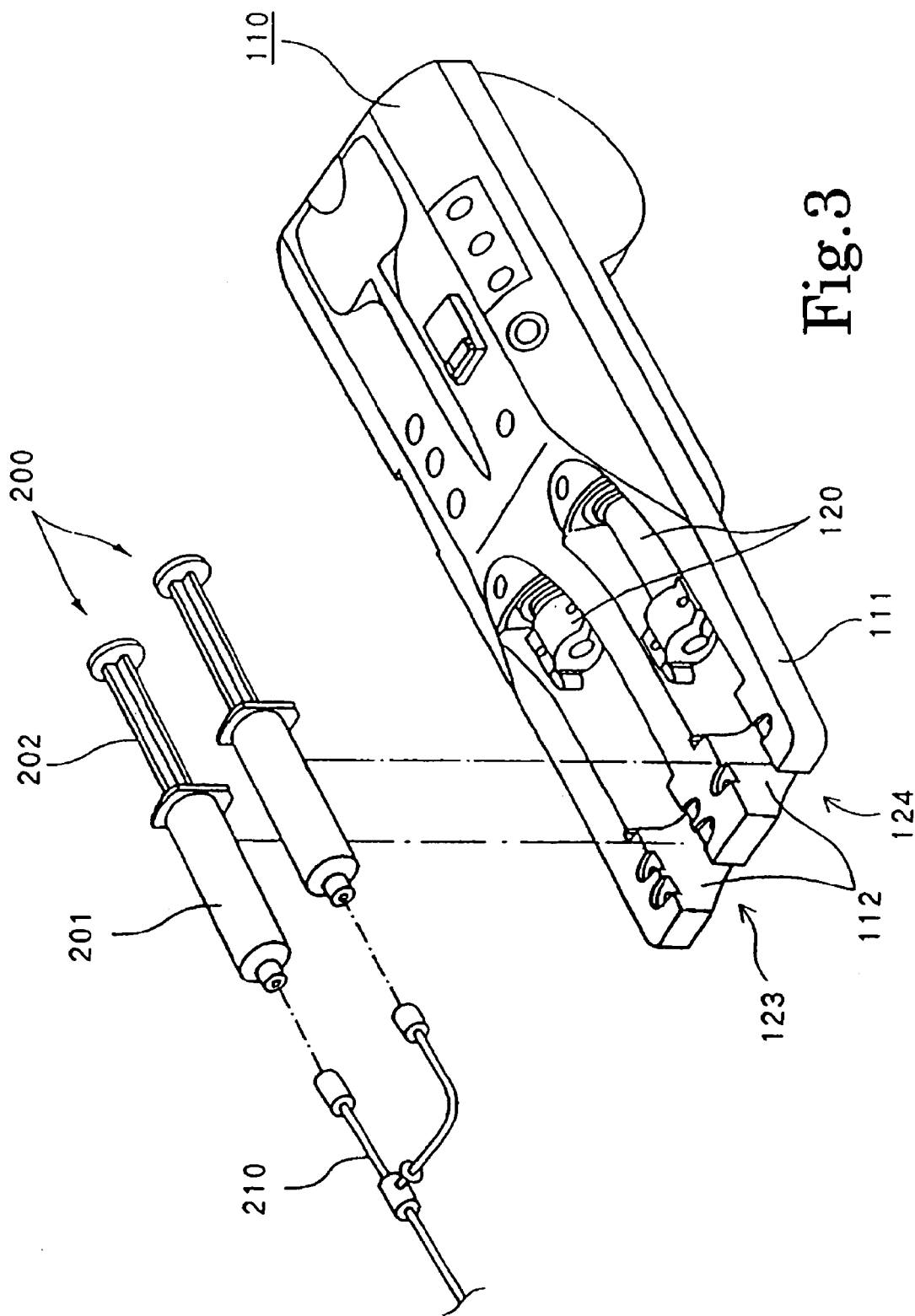
FIG. 3 is a perspective view of the liquid injector, showing the manner in which liquid syringes are set on an injection head of the liquid injector.

As shown in FIG. 3, injection head 110 has two recesses 112 defined as a syringe holding mechanism in an upper surface of syringe holder 111. Cylinders 201 of liquid syringes 220 are removably held in respective recesses 112. Each liquid syringe 220 comprises cylinder 201 and piston 202 slidably inserted in cylinder 201.

Two syringe actuating mechanisms 120 as injection performing means are disposed respectively behind recesses 112 in injection head 110 for individually gripping and sliding pistons 202 of syringes 200 that are held in respective recesses 112.

Each of syringe actuating mechanisms 120 has drive motor 121 (see FIG. 2) such as an ultrasonic motor or the like as a drive source for sliding piston 202 back and forth through a screw mechanism (not shown) or the like. Syringe actuating mechanisms 120 also have respective load cells 122 as pressure-sensitive devices for individually detecting pressures under which pistons 202 of syringes 200 are pressed.

Liquid syringe 200 which is filled with a contrast medium as a liquid and another liquid syringe 200 which is filled with a saline solution as another liquid are set respectively in two recesses 112 in injection head 110. Two recesses 112 and two syringe actuating mechanisms 120 make up liquid injection mechanisms including medium injection mechanism 123 for injecting a contrast medium into a subject and solution injection mechanism 124 for injecting a saline solution into a subject.

Figure 5:
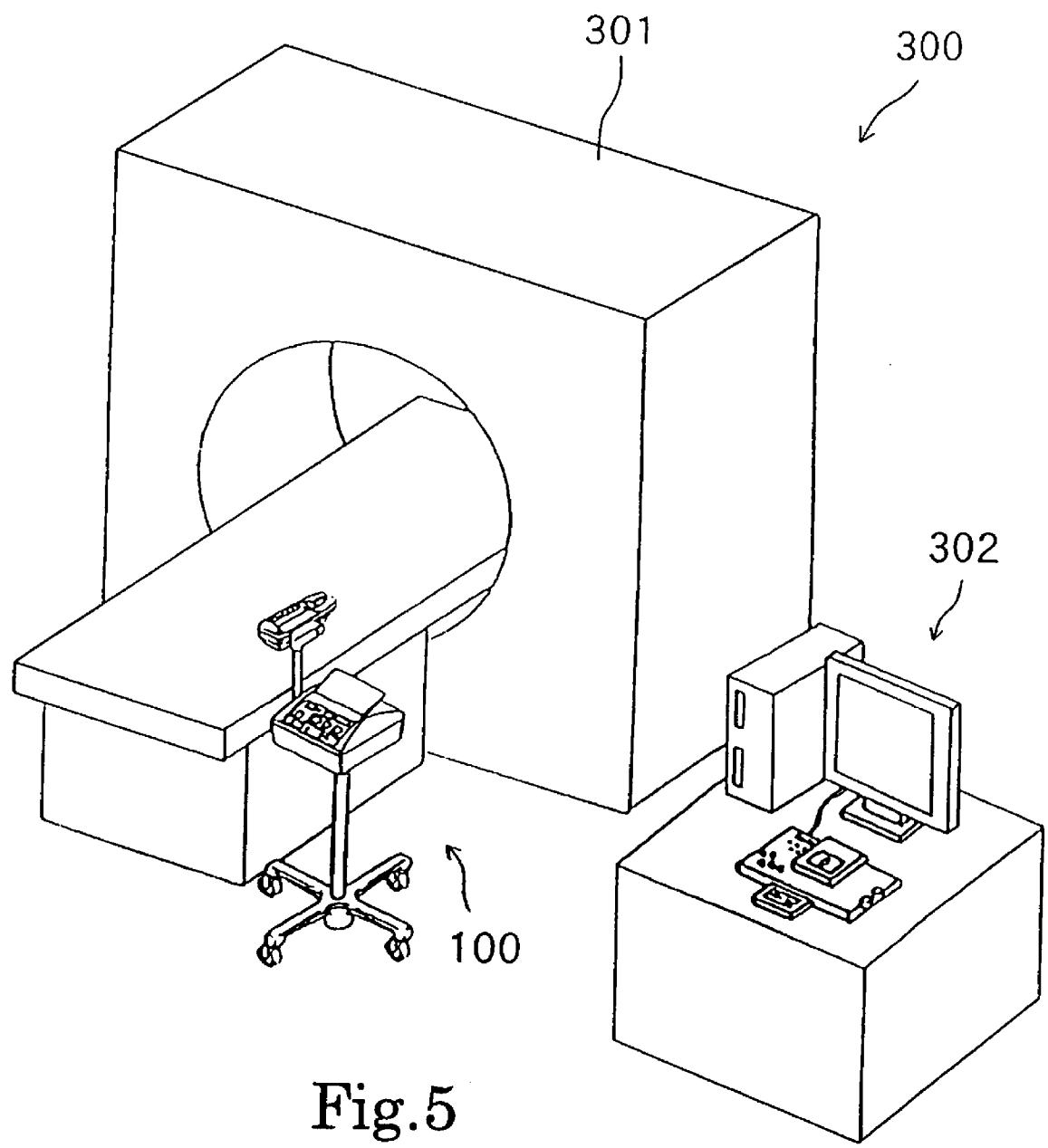
FIG. 5 is a perspective view of a CT scanner as an imaging diagnostic apparatus.

As shown in FIG. 5, liquid injector 100 is positioned near CT scanner 300 which serves as an imaging diagnostic apparatus. Liquid injector 100 injects a contrast medium and a saline solution into a subject who is to be imaged by CT scanner 300. CT scanner 300 has imaging unit 301 and control unit 302 which is connected on-line to liquid injector 100.

Figure 2:
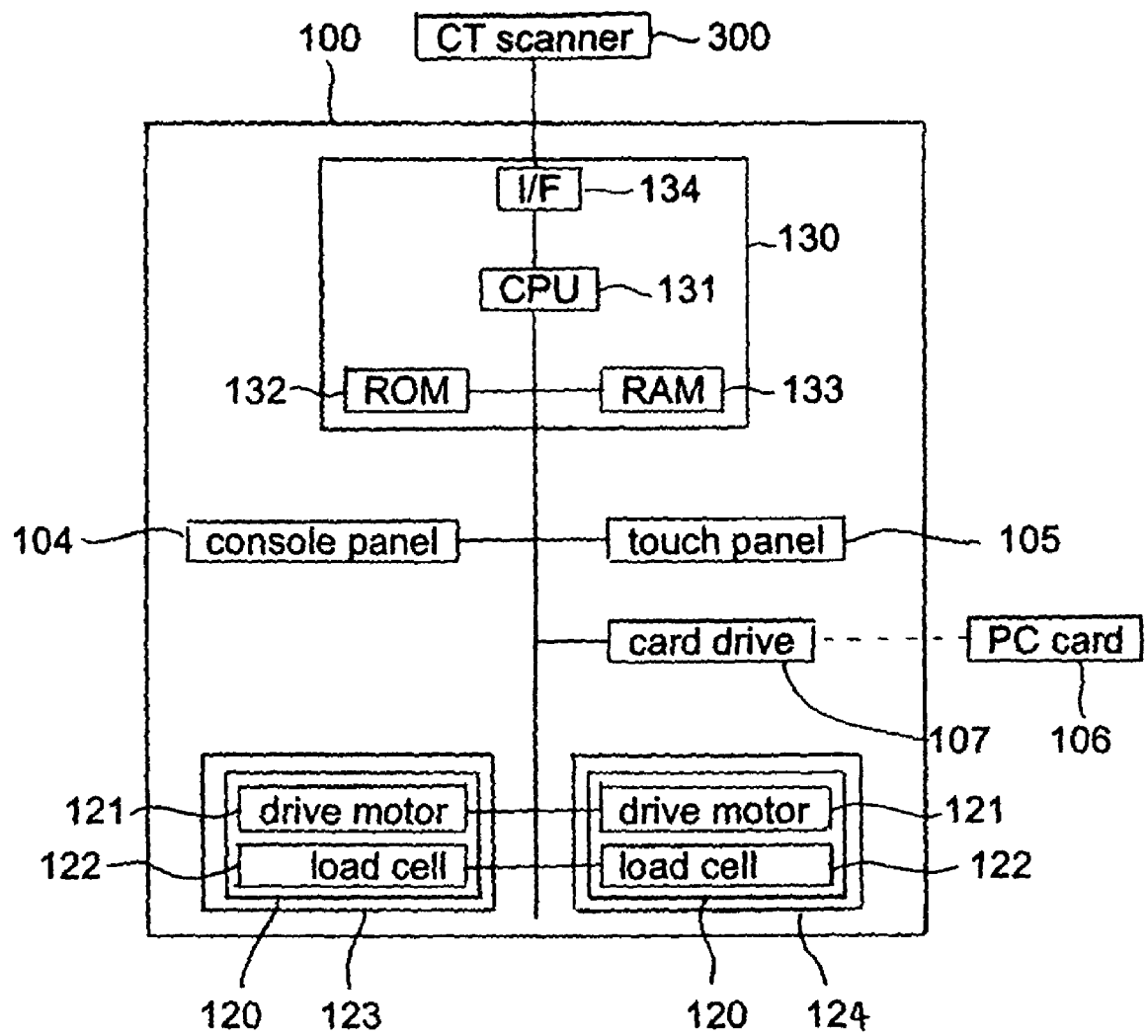
FIG. 2 is a block diagram of a circuit arrangement of the liquid injector.

As shown in FIG. 2, liquid injector 100 has computer unit 130 connected to drive motors 121 of two syringe actuating mechanisms 120, console panel 104, and touch panel 105.

Computer unit 130 comprises a so-called one-chip microcomputer, and has pieces of hardware including CPU (Central Processing Unit) 131, ROM (Read Only Memory) 132, RAM (Random Access Memory) 133, and I/F (Interface) 134. Computer unit 130 has a suitable computer program installed in the form of firmware in an information storage medium such as ROM 132. CPU 131 performs various processing operations according to the installed computer program.

Figure 1:
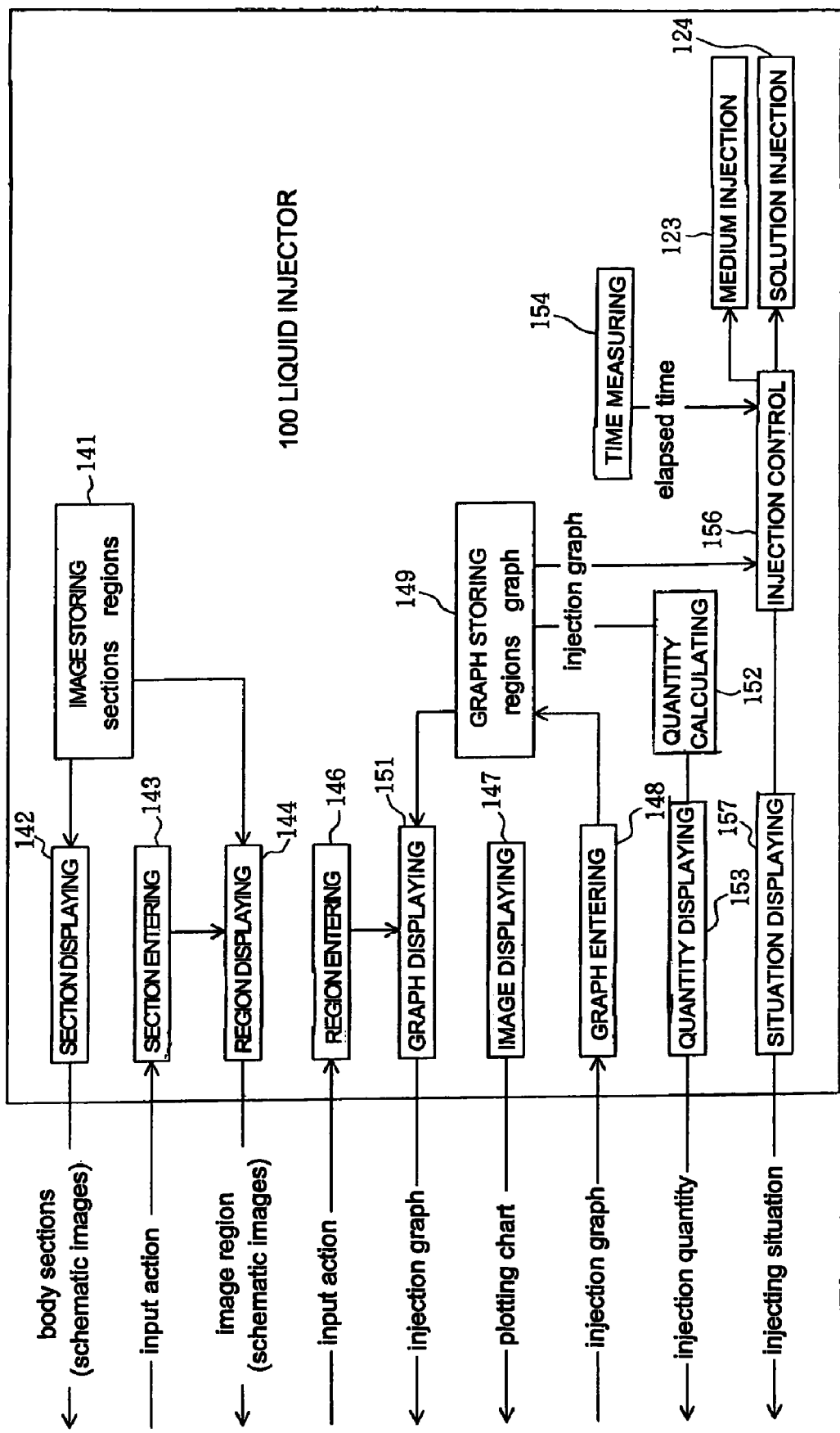
FIG. 1 is a block diagram showing a logic structure of a liquid injector according to an embodiment of the present invention.

By operating according to the installed computer program, computer unit 130 logically has various functions as various means which include, as shown in FIG. 1, image storing function 141, section displaying function 142, section entering function 143, region displaying function 144, region entering function 146, image displaying function 147, graph entering function 148, graph storing function 149, graph displaying function 151, quantity calculating function 152, quantity displaying function 153, time measuring function 154, injection control function 156, situation displaying function 157, etc.

Storing functions 141, 149 correspond to storage areas set up in RAM 133 for CPU 131 to recognize data stored therein according to the computer program. Displaying functions 142, 144, 147, 151, 153, 157 correspond to functions of CPU 131 to display stored data from RAM 133 on touch panel 105. Entering functions 143, 146, 148 correspond to functions of CPU 131 to recognize data based on input actions on touch panel 105. Other various functions 152, 154, 156 correspond to functions of CPU 131 to process data.

Image storing function 141 stores data of schematic images of a plurality of body sections of a human body and data of schematic images of a number of regions to be imaged in relation to each other. Section displaying function 142 displays schematic images of body sections whose data are stored by image storing function 141 in the shape of a human body.

Section entering function 143 accepts an input action to select one of the body sections displayed by section displaying function 142. Region displaying function 144 displays a schematic image of at least one region to be imaged which corresponds to the body section selected by section entering function 143. Region entering function 146 accepts an input action to select the region to be imaged whose image has been displayed by region displaying function 144.

More specifically, liquid injector 100 defines "head part, chest part, abdomen part, and leg part" as a plurality of body sections, and data of schematic images corresponding to those body sections are registered in ROM 132. When a certain action is performed on liquid injector 100, schematic images of "head part, chest part, abdomen part, and leg part" in association with body shapes are displayed on an upper screen area of touch panel 105, as shown in FIG. 6.

Data of schematic images of "brain part, jaw part, and neck part" are registered as a plurality of regions to be imaged in relation to the schematic image of the body section "head part". Similarly, data of schematic images of "heart part and lung part" are registered in relation to the schematic image of the body section "chest part", data of schematic images of "stomach part, liver part, . . . " are registered in relation to the schematic image of the body section "abdomen part", and data of images of "upper part and lower part" are registered in relation to the schematic image of the body section "leg part".

Figure 6:
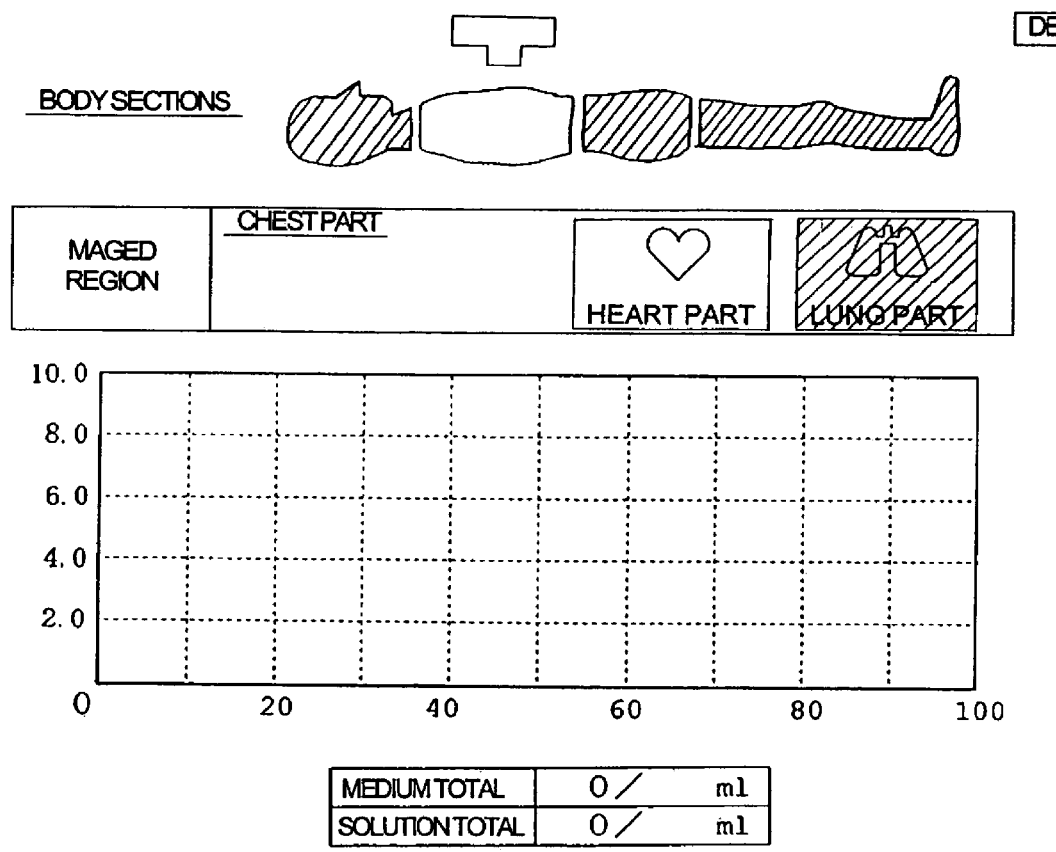
FIG. 6 is a schematic front elevational view showing an initial displayed image on a touch panel.

When one of the schematic images of the body sections displayed as a human body shape on touch panel 105 is manually acted upon, a schematic image of a scanner mechanism is displayed above only the schematic image that is acted upon, and that schematic image is highlighted with the other schematic images darkened, as shown in FIG. 6. At the same time, the schematic images of the regions that are related to the highlighted image are displayed below the displayed schematic images of the body sections. When one of the displayed schematic images of the related regions is manually acted upon, that schematic image is highlighted with the other schematic images darkened, as shown in FIG. 6.

Image displaying function 147 displays a plotting chart image having a vertical axis representative of liquid injection rates and a horizontal axis representative of liquid injection times. Graph entering function 148 accepts an input action to enter an injection graph of liquid injection rates at respective liquid injection times into the plotting chart image. Graph storing function 149 stores data of the entered injection graph for each region to be imaged. Graph displaying function 151 displays the injection graph represented by the stored data for each region to be imaged on the plotting chart image.

Figure 7:
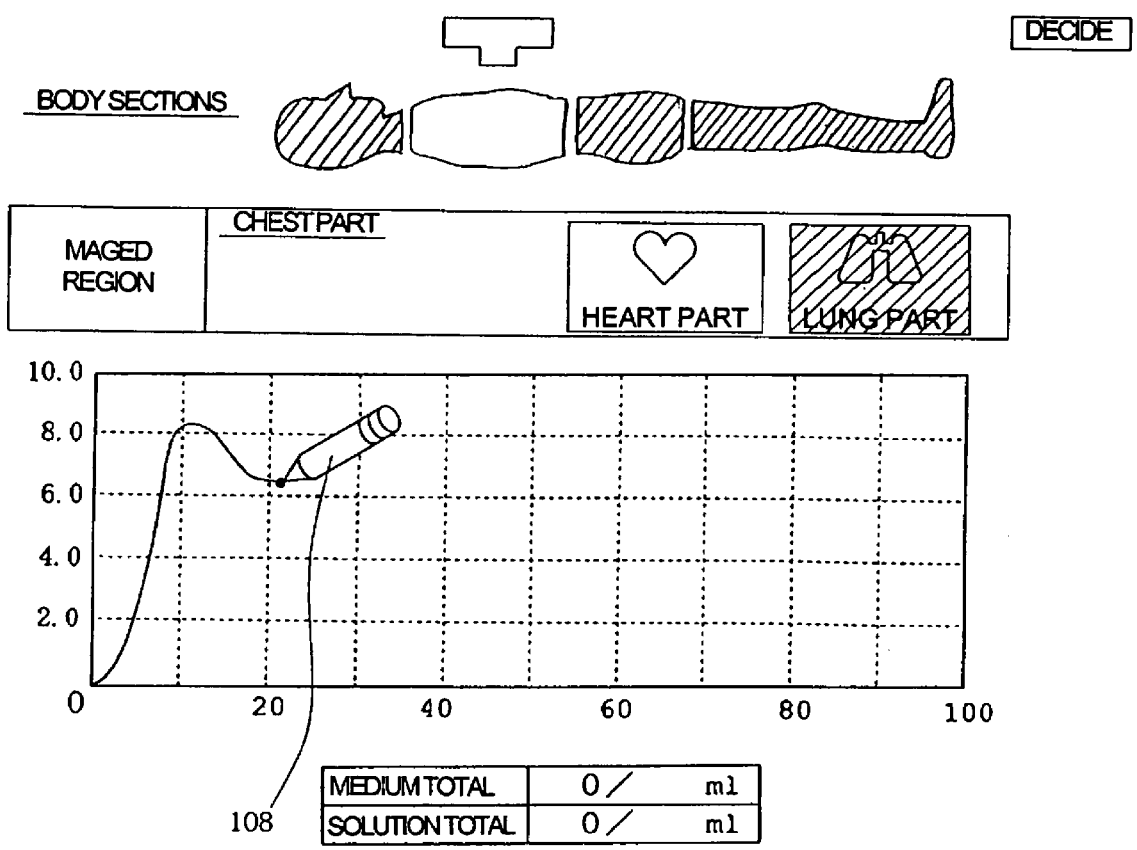
FIG. 7 is a schematic front elevational view showing a displayed image at the time an injection graph for a contrast medium is being entered.
Figure 8:
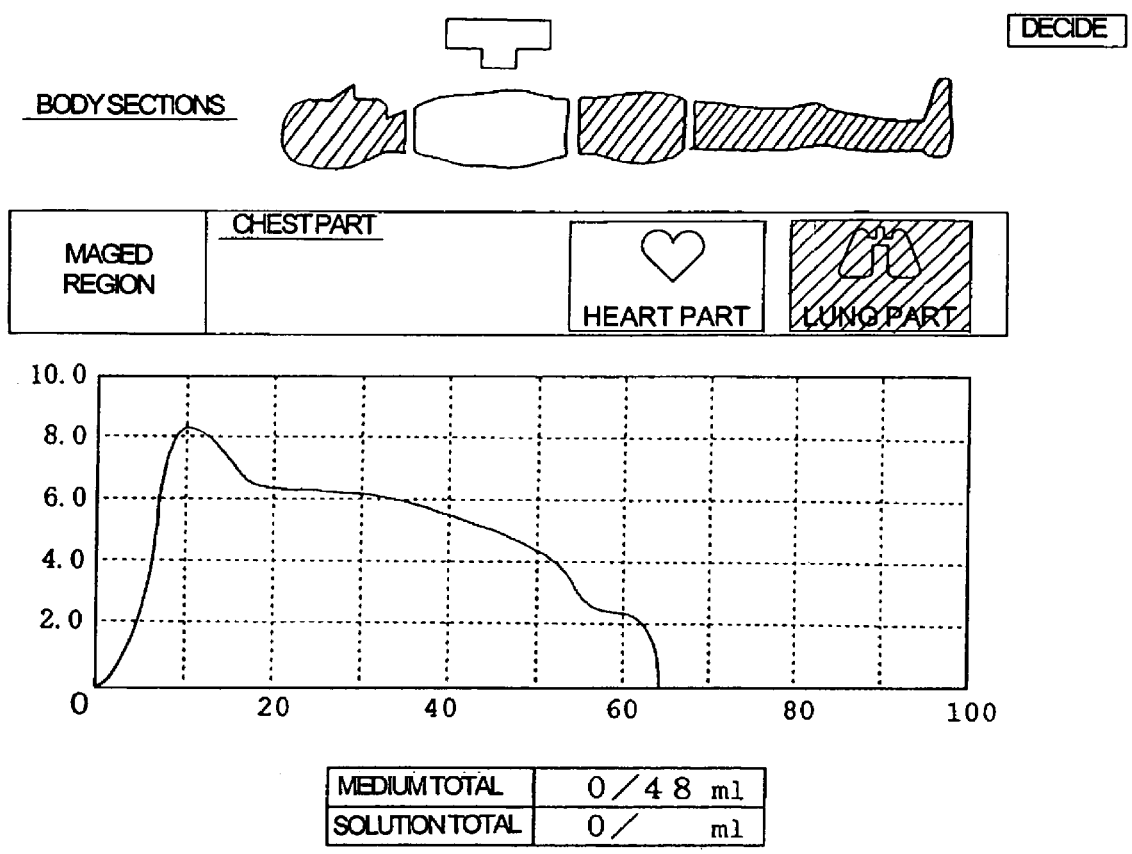
FIG. 8 is a schematic front elevational view showing a displayed image at the time an injection graph for a contrast medium has been entered.
Figure 9:
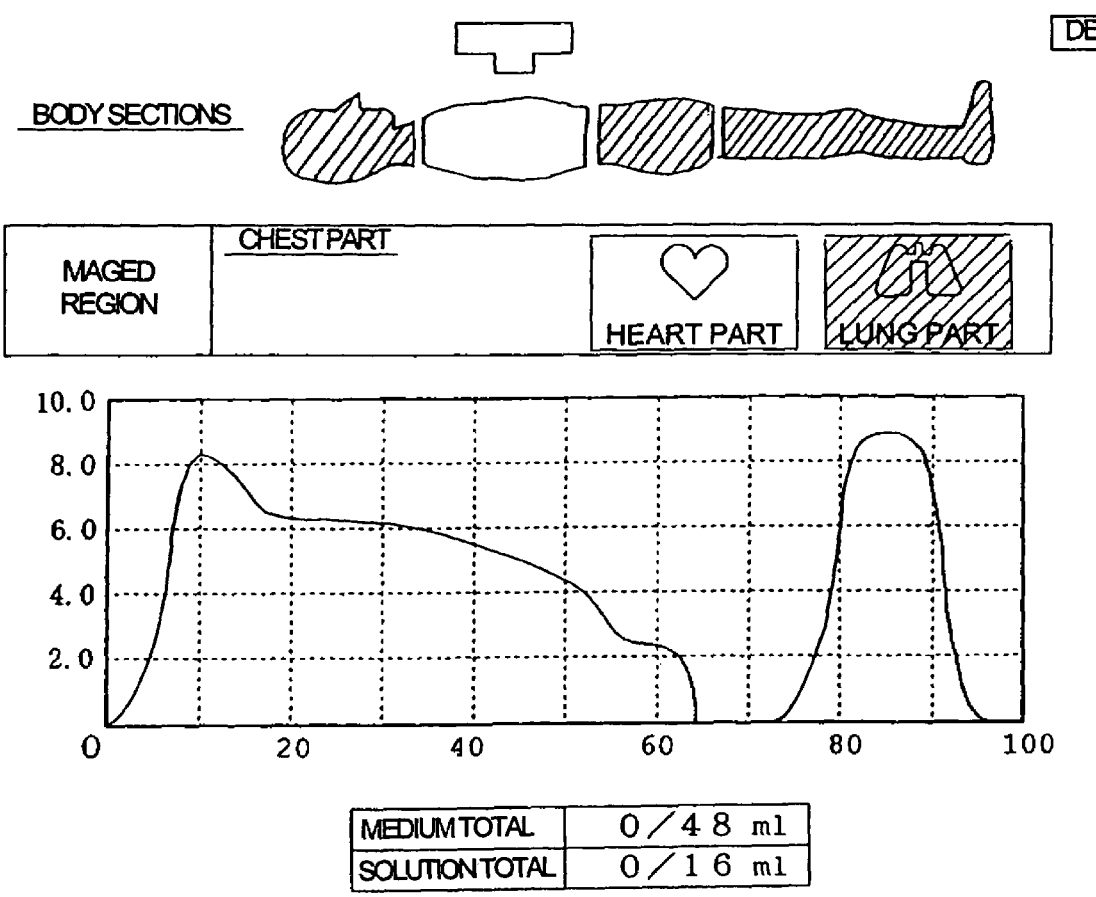
FIG. 9 is a schematic front elevational view showing a displayed image at the time an injection graph for a saline solution has also been entered.

More specifically, liquid injector 100 displays, on touch panel 105, the plotting chart image below the displayed schematic images of the regions to be imaged. As shown in FIGS. 7 through 9, an injection graph for injecting a contrast medium or the like can be entered as a free curve into the plotting chart image by write pen 108 based on an input action made by the operator.

When an input action is applied to enter an injection graph while a region to be imaged has been selected, the data of the injection graph is registered in association with the displayed region to be imaged. When the region to be imaged is subsequently selected, the injection graph whose data is registered is displayed on the plotting chart image.

When the injection graph whose data is registered is displayed on the plotting chart image, the displayed injection graph can freely be corrected by write pen 108 based on an input action made by the operator. The injection graph thus displayed can fully be erased, and a new injection graph can be entered by write pen 108 based on an input action made by the operator. The manufacturer of liquid injector 100 may register default data of recommended injection graphs before shipment of liquid injector 100, and may register data of custom-tailored injection graphs based on needs of the end user.

Injection graphs may be uploaded from RAM 133 to PC card 106 by card drive 107, and downloaded from PC card 106 to RAM 133 by card drive 107. As described in detail later on, since liquid injector 100 can inject a saline solution into the subject after it has injected a contrast medium into the subject, injection graphs for a contrast medium and a saline solution, which share injection times, may be entered as shown in FIG. 9.

Quantity calculating function 152 calculates a quantity to be injected of a liquid as the area of a chart portion surrounded by the entered injection graph and the horizontal axis of the plotting chart image. Quantity displaying function 153 displays the quantity of the liquid to be injected. Specifically, as shown in FIGS. 8 and 9, when both ends of an entered injection graph reaches the horizontal axis of the plotting chart image, a quantity to be injected of a liquid such as a contrast medium or a saline solution is calculated from the area of a chart portion surrounded by the entered injection graph and the horizontal axis of the plotting chart image. The calculated quantity is then displayed as numerical data below the plotting chart image. If an injection graph, both ends of which do not reach the horizontal axis of the plotting chart image is entered, then the ends are vertically extended to the horizontal axis of the plotting chart image, and a quantity to be injected of a liquid is then calculated as the area of a chart portion surrounded by the entered injection graph and the horizontal axis of the plotting chart image.

Time measuring function 154 measures a time that has elapsed from the start of injection of a liquid. Injection control function 156 controls, in real-time, operation of syringe actuating mechanism 120 according to a measured time and an injection graph whose data has been stored. If the data of both injection graphs for a contrast medium and a saline solution are registered so as to share injection times as described above, then injection control function 156 controls operation of medium injection mechanism 123 and solution injection mechanism 124 in an interlinked fashion according to the injection graphs for the contrast medium and the saline solution.

Figure 10:
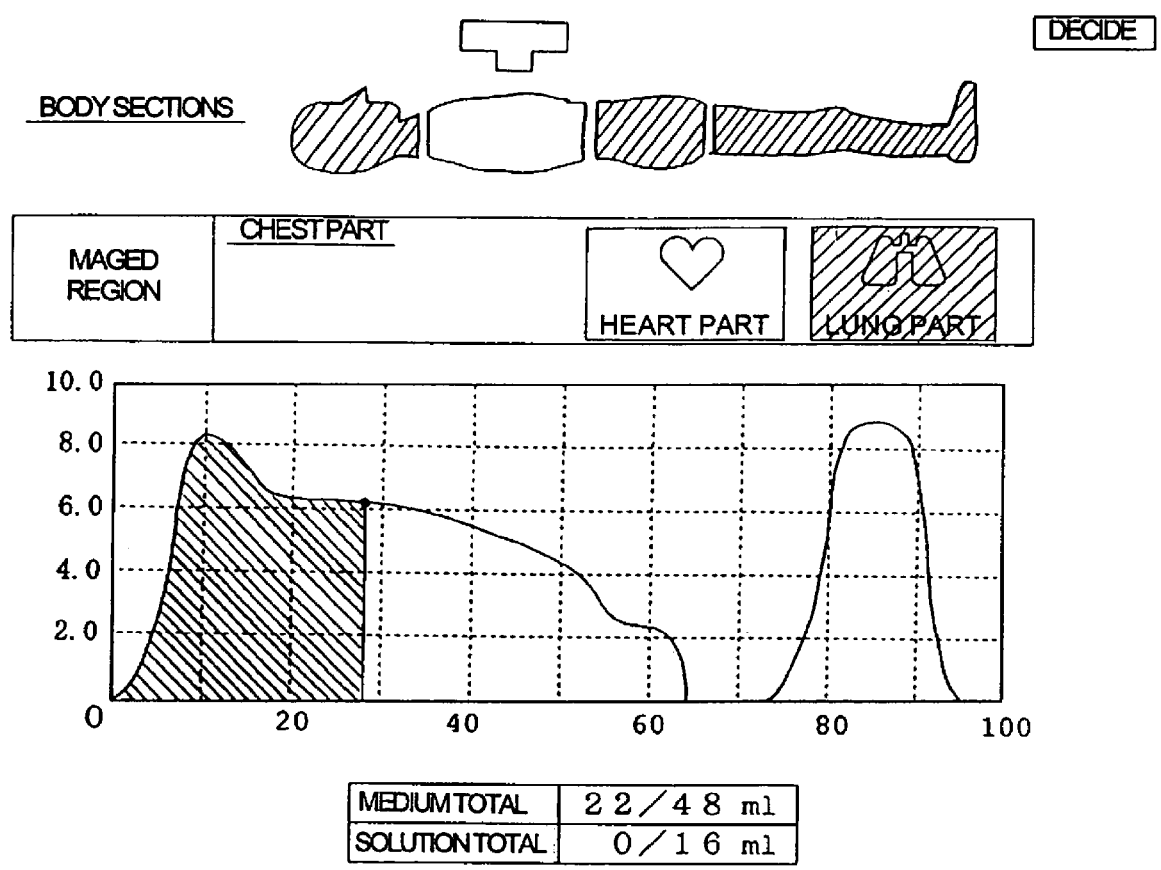
FIG. 10 is a schematic front elevational view showing a displayed image at the time an injection process is being carried out.

As shown in FIG. 10, situation displaying function 157 displays, in a reversed mode, a chart portion surrounded by the injection graph, the horizontal axis, and a vertical line, and also displays total quantities to be injected as fractions, for thereby displaying injecting situations of medium injection mechanism 123 and solution injection mechanism 124 in real-time.

While the above various functions of liquid injector 100 are accomplished by pieces of hardware such as console panel 104, if necessary, they are mainly implemented by CPU 131 as a piece of hardware as it functions according to resources stored in an information storage medium such as ROM 132, etc., and the computer program.

Such resources include a data file of schematic images of a plurality of body sections of a human being and schematic images of a number of regions to be imaged in relation to each other, a data file of injection graphs for medium injection mechanism 123 and solution injection mechanism 124 for each of the human body regions to be imaged, etc.

The above computer program is stored in an information storage medium such as RAM 133 or the like as software to be executed by CPU 131 for displaying schematic images of a plurality of body sections whose data have been registered in RAM 133, for example, in the shape of a human body on touch panel 105, receiving an input action made on touch panel 105 to select one of the displayed body sections, displaying a schematic image of at least one region to be imaged which corresponds to the selected body section, receiving an input action to select the region to be imaged whose image has been displayed, displaying an injection graph whose data has been registered, together with a plotting chart image, in association with the selected region, displaying a blank plotting chart image if the data of an injection graph associated with the selected region has not been registered, receiving an input action to enter an injection graph into the plotting chart image with write pen 108, storing the data of the entered injection graph in association with a corresponding region to be imaged, calculating a quantity to be injected of a liquid as the area of a chart portion surrounded by the entered injection graph and the horizontal axis of the plotting chart image, displaying data of the calculated quantity, measuring a time that has elapsed from the start of injection of the liquid, controlling operation of medium injection mechanism 123 and solution injection mechanism 124 in an interlinked fashion according to the injection graphs, whose data have been stored, for the contrast medium and the saline solution and the measured time that has elapsed, and displaying injecting situations in real-time.

Operation of the Liquid Injector

For using liquid injector 100 of the above construction, the operator (not shown) positions liquid injector 100 near imaging unit 301 of CT scanner 300 as shown in FIG. 5. Then, as shown in FIG. 3, the operator connects two liquid syringes 200 to the subject (not shown) placed in imaging unit 301 with bifurcated extension tube 210. Cylinders 201 of liquid syringes 200 are held in respective recesses 122 of injection head 110, and pistons 202 are gripped by syringe actuating mechanisms 120.

Figure 11:
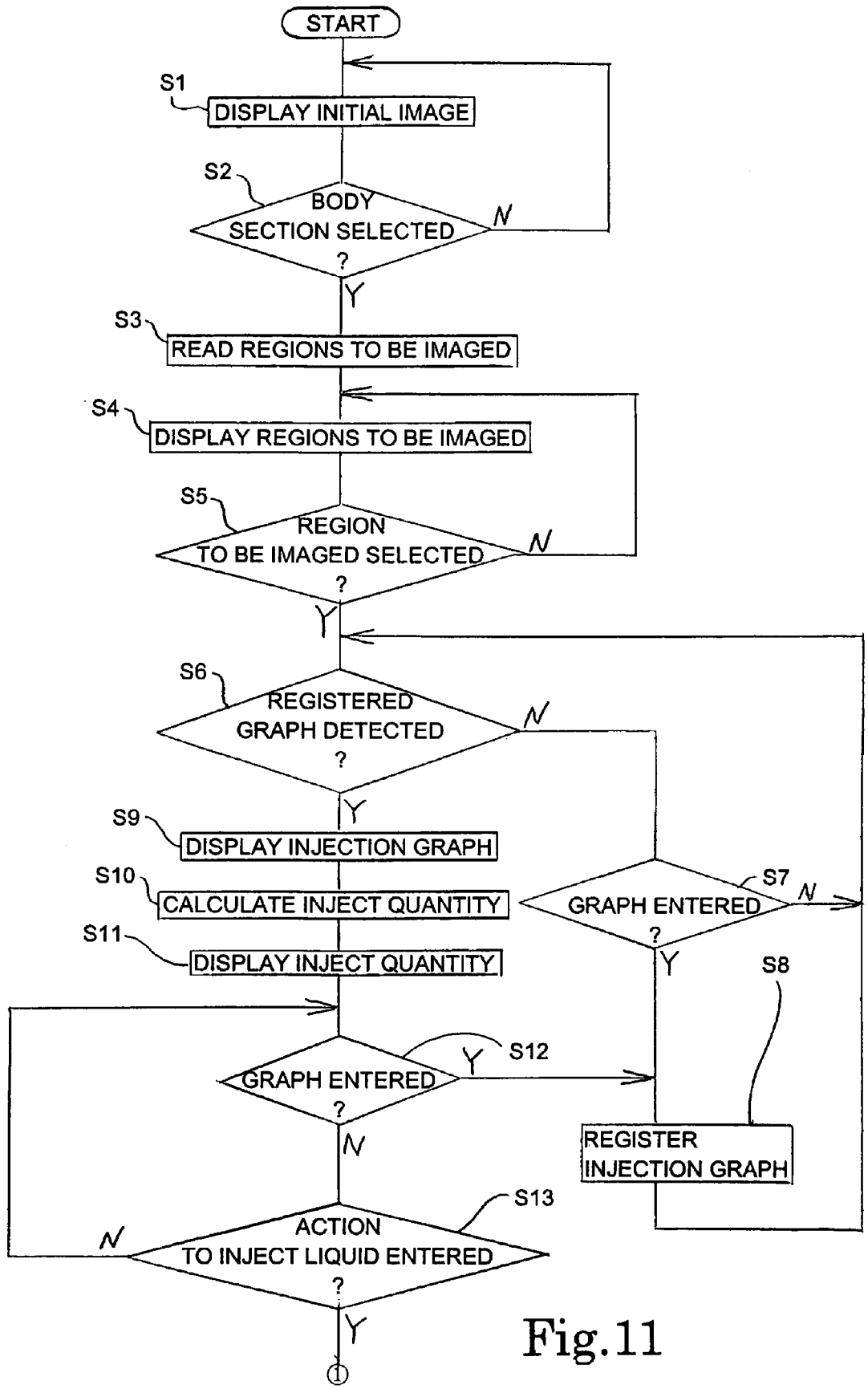
FIG. 11 is a flowchart of a former part of a processing sequence of the liquid injector.

Then, the operator makes an input action on console panel 104 to instruct liquid injector 100 to start operating. Touch panel 105 then displays an initial image on its display screen in step S1 shown in FIG. 11. As shown in FIG. 6, the initial image contains various input items arranged successively downwardly according to an input sequence. The initial image includes in its uppermost portion schematic images of a plurality of body sections in the shape of a human body.

If the operator touches, with a fingertip, one of the schematic images of the body sections displayed on touch panel 105 to select the touched schematic image of the body section in step S2, then, as shown in FIG. 6, the selected schematic image of the body section is highlighted with the other schematic images darkened, and a schematic image of a scanner mechanism is also displayed above the selected schematic image of the body section.

At the same time, schematic images of a plurality of regions to be imaged which are related to the selected body section are read and displayed below the displayed schematic images of the body sections in steps S3, S4. If the operator touches one of the schematic images of the regions to select the touched schematic image of the region in step S5, then only the selected schematic image of the region is highlighted with the other schematic images darkened, as shown in FIG. 6.

When the region to be imaged is thus selected, liquid injector 100 confirms whether the data of an injection graph associated with the selected region is registered in RAM 133 or not in step S6. If the data is registered in RAM 133, then the injection graph is displayed on a plotting chart image in step S9 as shown in FIG. 9.

If the data is not registered in RAM 133, then the plotting chart image is left blank, allowing the operator to enter an injection graph therein. For example, the operator makes a certain action on console panel 107, bringing that liquid injector 100 into a state for entering an injection graph for a contrast medium. As shown in FIGS. 7 and 8, the operator enters a free curve on touch panel 105 with write pen 108 in step S7. The data of the entered curve is registered as an injection graph for a contrast medium for the selected region to be imaged in step S8.

If the operator wants to inject a saline solution after having injected a contrast medium, the operator thereafter makes a certain action on console panel 107, bringing that liquid injector 100 into a state for entering an injection graph for a saline solution. Then, as shown in FIG. 9, the operator enters a free curve on touch panel 105 with write pen 108 in step S7. The data of the entered curve is registered as an injection graph for a saline solution for the selected region to be imaged in step S8.

In this case, the injection graph for the contrast medium and the injection graph for the saline solution share injection times. In actual operation, after the contrast medium is injected, the saline solution is injected. In FIG. 9, a certain interval is present between the end of the injection graph for the contrast medium and the start of the injection graph for the saline solution. Therefore, the saline solution starts being injected after elapse of a predetermined time from the completion of the injection of the contrast medium.

The injection graphs can freely be entered into liquid injector 100. For example, if the end of an injection graph for a contrast medium and the start of an injection graph for a saline solution coincide with each other, then the saline solution starts being injected at the same time that the injection of the contrast medium is completed in actual operation. If the start of an injection graph for a saline solution precedes the end of an injection graph for a contrast medium, then the saline solution starts being injected immediately before the injection of the contrast medium is completed in actual operation.

After injection graphs are displayed on the plotting chart image in step S9, quantities of a contrast medium and a saline solution to be injected are calculated as the areas of chart portions surrounded by the entered injection graphs and the horizontal axis in step S10. Then, the calculated quantities to be injected are displayed as numerical values below the plotting chart image in step S11, as shown in FIG. 9.

Figure 12:
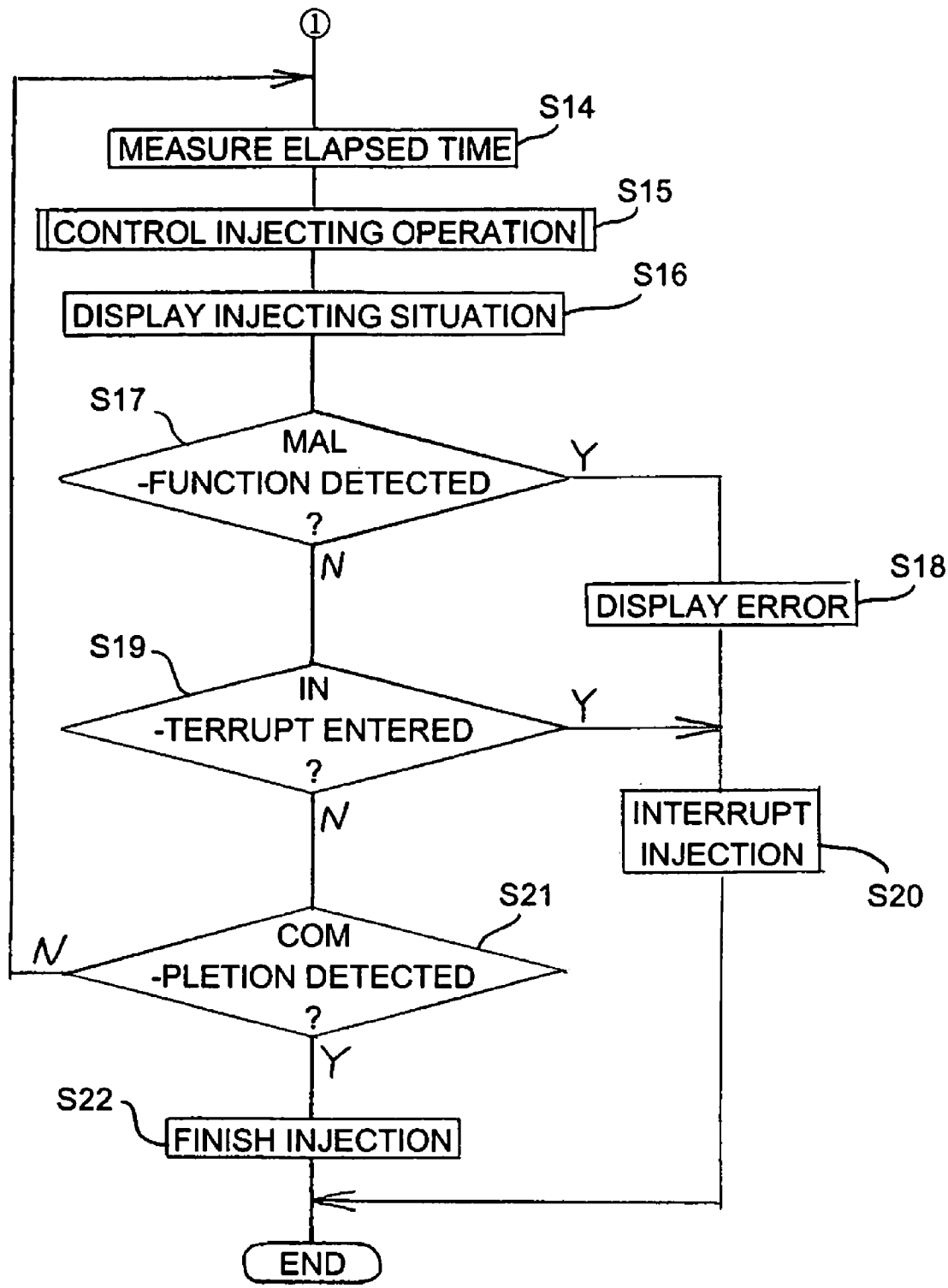
FIG. 12 is a flowchart of a latter part of the processing sequence of the liquid injector.

Even after the injection graphs and the quantities to be injected are displayed in steps S9-S11, the operator may correct the injection graphs if desired in step S12. If after having confirmed the injection graphs, the operator makes an input action on console panel 104 to carry out an injection process in step S13, then medium injection mechanism 123 and solution injection mechanism 124 are controlled in operation according to the injection graphs and the time that has elapsed in steps S14, S15 shown in FIG. 12.

As medium injection mechanism 123 and solution injection mechanism 124 operate, a portion surrounded by the injection graph, the horizontal axis, and a vertical line is displayed in reverse, and the quantity of a liquid that has been injected so far is displayed as a numerical value in comparison with the total quantity to be injected. Thus, injecting situations of medium injection mechanism 123 and solution injection mechanism 124 are displayed in real-time in step S16.

During the above injection process in steps S14 through S21, if a malfunction is detected based on the injection pressures in step S17, then an error is displayed as a guidance image on touch panel 105 in step S18, and the injection process is interrupted in step S20.

If the operator makes an input action on touch panel 105 to interrupt the injection process in step S19, then the injection process is also interrupted in step S20. After liquid injector 100 has injected the set quantities of contrast medium and saline solution, liquid injector 100 finishes the injection process, and returns to its initial state in step S22.

Advantages of the Liquid Injector

When a desired injection graph is entered into a plotting chart image displayed on touch panel 105 by write pen 108, liquid injector 100 changes a liquid injection rate with time according to the entered injection graph. Therefore, a complex liquid injection process for injecting a liquid at a chronologically changing injection rate can be carried out through simple input actions.

Since a complicated injection graph for keeping the image contrast of a fluoroscopic image based on a contrast medium approximately at an appropriate level can simply be entered into liquid injector 100, it is possible to allow CT scanner 300 to capture a fluoroscopic image of good quality.

As an injection graph is manually entered in touch panel 105 by write pen 108, a desired complex free curve can easily be entered as an injection graph. A quantity to be injected of a liquid is calculated as the area of a chart portion surrounded by an entered injection graph and the horizontal axis of the plotting chart image, and the data of the calculated quantity to be injected is displayed over the plotting chart image. Therefore, the operator can easily confirm the quantity to be injected of a liquid according to a complex injection graph.

Liquid injector 100 registers and reads data of injection graphs for respective regions to be imaged of a human body. Therefore, liquid injector 100 can inject a liquid into a subject according to an injection graph optimum for a desired region whose fluoroscopic image is to be captured by CT scanner 300.

Liquid injector 100 displays on its touch panel 105 schematic images of a plurality of body sections in the shape of a human body. When the operator manually touches and selects one of the schematic images of the body sections, schematic images of a plurality of regions to be imaged which are related to the selected body section are displayed. Then, the operator manually touches and selects one of the schematic images of the regions to be imaged. Consequently, the operator can select, reliably through a simple action, a region to be imaged for which the data of an injection graph is to be registered and read.

Since liquid injector 100 displays schematic images of a plurality of body sections in the shape of a human body, the operator is allowed to select any of the body sections easily and reliably. Because schematic images of body sections and regions to be imaged are displayed on touch panel 105 and can directly be manually acted upon, they can be touched and selected easily and reliably.

With liquid injector 100, medium injection mechanism 123 and solution injection mechanism 124 are operated to inject a contrast medium and a saline solution into the subject. Inasmuch as medium injection mechanism 123 and solution injection mechanism 124 are automatically interlinked according to entered injection graphs, the contrast medium and the saline solution can be injected into the subject in interlinked relation to each other without the need for a complex control process. As liquid injecting situations are displayed in real-time, the operator can confirm the liquid injecting situations in real-time.

Liquid injector 100 is capable of uploading an entered injection graph to PC card 106 and downloading an entered injection graph from PC card 106. Therefore, liquid injector 100 can switch optimum injection graphs for respective operators and subjects.

Modifications of the Liquid Injector

The present invention is not limited to the above embodiment, but various changes or modifications may be made therein without departing from the scope of the invention. For example, although liquid injector 100 according to the above embodiment has medium injection mechanism 123 and solution injection mechanism 124 which have respective syringe actuating mechanisms 120 for injecting a contrast medium and a saline solution, the present invention is also applicable to a liquid injector having a single liquid injection mechanism for injecting a contrast medium only.

In the above embodiment, an injection graph is entered and displayed simultaneously on touch panel 105. However, an injection graph may be entered and displayed individually on a pointing device and a display panel, respectively, (not shown) which are independent of each other.

In the above embodiment, a plotting chart image whose data is electronically registered is displayed on touch panel 105. However, a plotting chart may be fixedly formed, as by painting, on the surface of touch panel 105 at a suitable position thereon.

In the above embodiment, a free curve is entered as an injection graph. However, a plurality of successive straight lines may be entered as an injection graph, and may be converted into a free curve. Furthermore, a plurality of passing points entered as an injection graph may be successively joined to convert themselves into a plurality of straight lines, and the data of a free curve successively passing through such a plurality of passing points may be generated.

Figure 13:
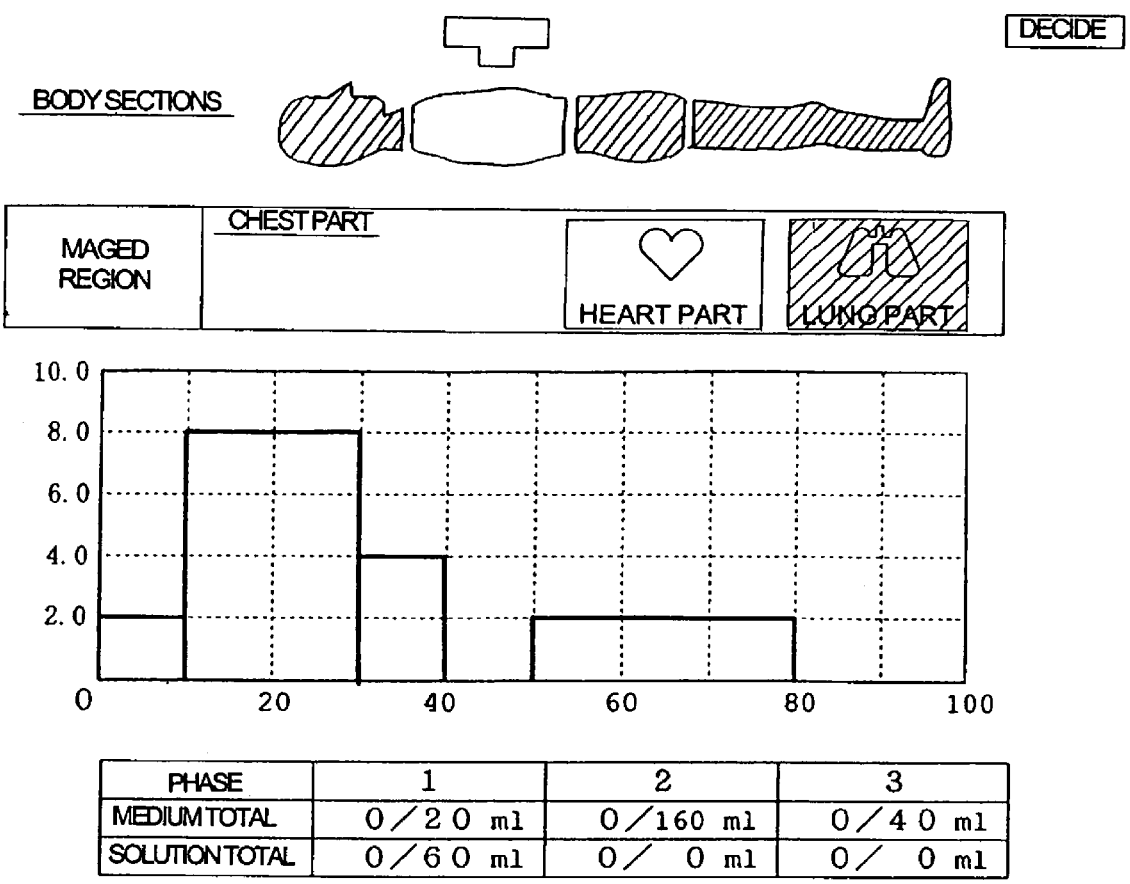
FIG. 13 is a schematic front elevational view showing a displayed image on a touch panel according to a first modification of the present invention.

As shown in FIG. 13, a plurality of rectangular regions may be entered as an injection graph, and a quantity to be injected of a liquid may be calculated as the area of each of the rectangular regions. If an injection graph is entered as rectangular regions, then each of the rectangular regions may preferably be edited by vertically moving the upper side of the rectangular region and horizontally moving the right side of the rectangular region.

Figure 14:
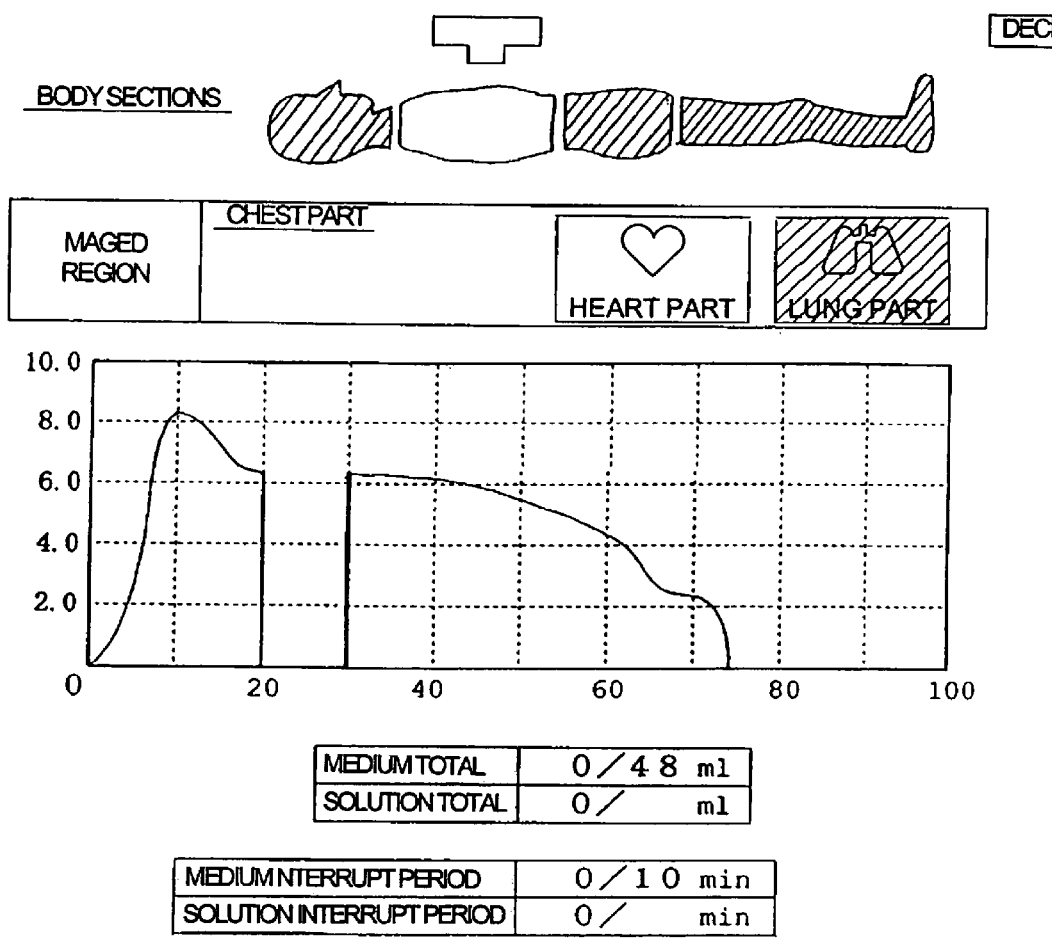
FIG. 14 is a schematic front elevational view showing a displayed image on a touch panel according to a second modification of the present invention.

As shown in FIG. 14, a period of time for interrupting the injection of a liquid may be entered in a displayed injection graph. Each of syringe actuating mechanisms 120 may be controlled according to the injection graph and may be temporarily inactivated during the interrupting period of time. The remaining time of the interrupting period of time may be displayed in real-time.

In the above embodiment, when an injection graph representing a liquid injection rate at each liquid injection time is entered into a plotting chart image having a vertical axis representative of liquid injection rates and a horizontal axis representative of liquid injection times, the actual liquid injection rate changes depending on the measured time that has elapsed, according to the entered injection graph. However, an injection graph representing a quantity to be injected of a liquid at each liquid injection time may be entered into a plotting chart image having a vertical axis representative of quantities to be injected of a liquid and a horizontal axis representative of liquid injection times, and the actual quantity to be injected of a liquid may be controlled depending on the measured time that has elapsed, according to the entered injection graph.

Figure 15:
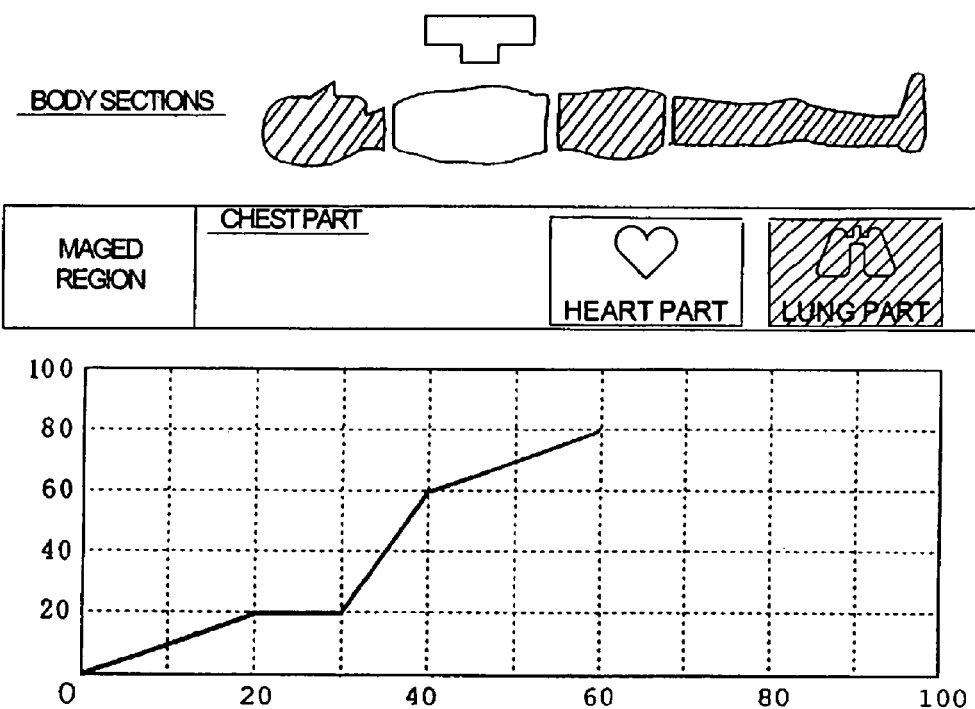
FIG. 15 is a schematic front elevational view showing a displayed image on a touch panel according to a third modification of the present invention.

For example, as shown in FIG. 15, if a quantity to be injected of a liquid changes linearly from 0 (ml.) to 20 (ml.) between liquid injection times of 0 (min.) and 20 (min.), then a liquid injection rate of 1.0 (ml./min.) is maintained from the start of injection up to the liquid injection time of 20 (min.), and the injected quantity reaches 20 (ml.) at the liquid injection time of 20 (min.).

If the quantity to be injected remains to be 20 (ml.) between liquid injection times of 20 (min.) and 30 (min.), then the liquid injection is interrupted between liquid injection times of 20 (min.) and 30 (min.). Since the illustrated injection graph has its terminal end positioned at a quantity to be injected of 80 (ml.) at a liquid injection time of 60 (min.), 80 (ml.) of the liquid is finally injected at the liquid injection time of 60 (min.).

An injection graph representing a liquid injection rate at each quantity to be injected of a liquid may be entered into a plotting chart image having a vertical axis representative of liquid injection rates and a horizontal axis representative of quantities to be injected of a liquid, and the actual liquid injection rate may be changed depending on the detected quantity to be injected of a liquid according to the entered injection graph.

Figure 16:
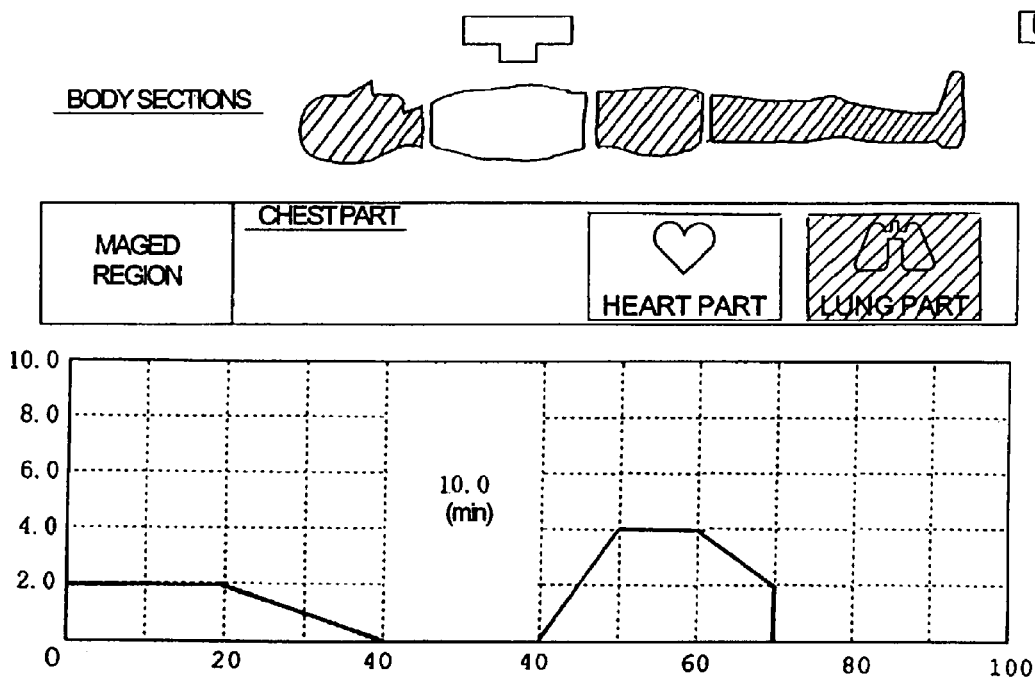
FIG. 16 is a schematic front elevational view showing a displayed image on a touch panel according to a fourth modification of the present invention.

For example, as shown in FIG. 16, if a liquid injection rate is 2.0 (ml./min.) between quantities to be injected of 0 (ml.) and 20 (ml.), then the liquid injection rate of 2.0 (ml./min.) is maintained until 20 (ml.) of a liquid is injected from the start of injection, and 20 (ml.) of the liquid is injected at a liquid injection time of 10 (min.).

If a liquid injection rate changes from 2.0 (ml./min.) to 0 (ml./min.) between quantities to be injected of 20 (ml.) and 40 (ml.), then the liquid injection rate is linearly reduced to 0 (ml./min.) while the liquid injected up to 20 (ml.) is further injected up to 10 (ml.).

Since an interrupting period of 10 (min.) occurs when the injected quantity is 40 (ml.), the liquid injection is interrupted for 10 (min.) when the liquid is injected up to 40 (ml.). The illustrated injection graph has a blank interval along the horizontal axis for the interrupting period.

In the above embodiment, the data of an injection graph for each region to be imaged is registered, and then read for a desired region to be imaged for controlling the injection of a liquid. There are various other conditions than the selection of a region to be imaged for an optimum injection of a liquid such as a contrast medium.

For example, the actual contrast medium for use on CT scanner 300 contains an effective component of iodine whose concentration differs from product to product. Imaging conditions differ with body weights of subjects to be imaged. As disclosed in Japanese patent application No. 2003-039756 filed by the present applicant, the data of the weight of a subject and the type of a contrast medium used may be entered into the liquid injector, and an injection graph may be adjusted depending on the entered data.

In the above embodiment, a contrast medium and a saline solution are sequentially injected according to an injection graph. However, as disclosed in Japanese patent application No. 2002-363675, it is possible to dilute a contrast medium with a saline solution and inject the diluted contrast medium according to an injection graph.

In the above embodiment, an injection graph can be downloaded from PC card 106 as an information storage medium to liquid injector 100. Various products may be used as such an information storage medium. Liquid injector 100 may not copy the data of an injection graph from PC card to RAM 133, but may read the data of an injection graph from loaded PC card 106 in real-time.

The data of an injection graph may be registered in an external database server, and liquid injector 100 may download the registered data on-line from the external database server. Similarly, the data of an injection graph may be registered in a host computer of the manufacturer of liquid injector 100, and liquid injector 100, which is installed in a medical facility, may download the registered data from the host computer through the Internet.

In the above embodiment, touch panel 105 is mounted on the upper surface of main body 103 of liquid injector 100, and injection head 110 is mounted on the upper end of movable arm 106 which is vertically mounted on the side wall of main body 103. However, as shown in FIGS. 17a and 17b, touch panel 105 may directly be connected to injection head 110 parallel thereto.

Figure 17A:
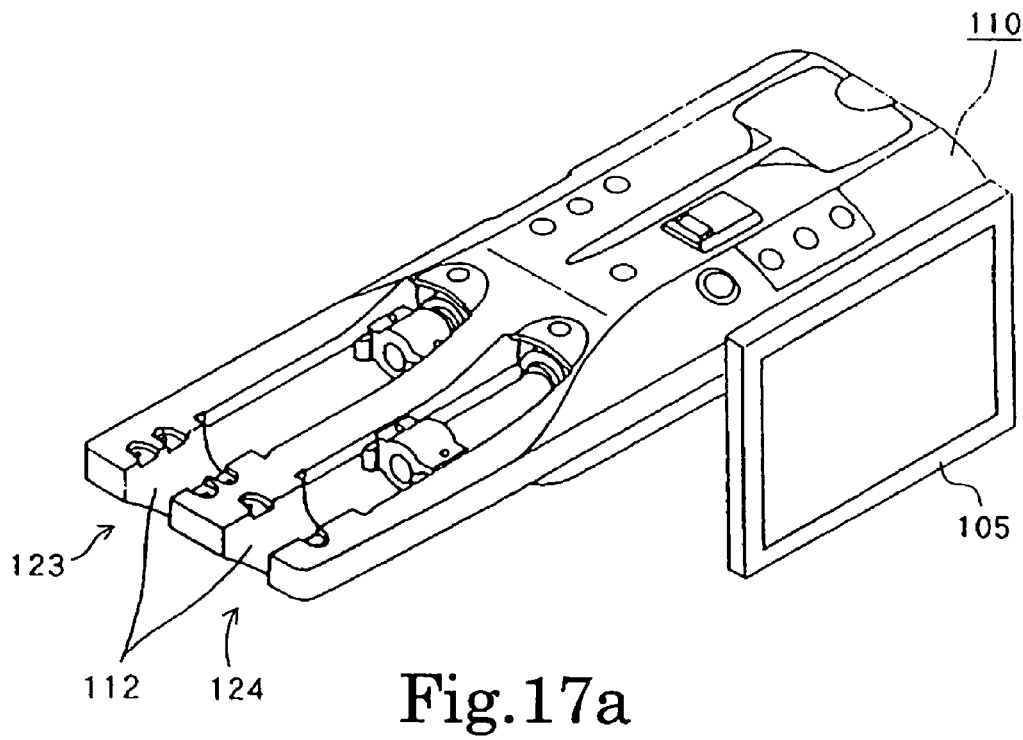
FIGS. 17a and 17b are perspective views showing injection heads according to a fifth modification of the present invention.
Figure 17B:
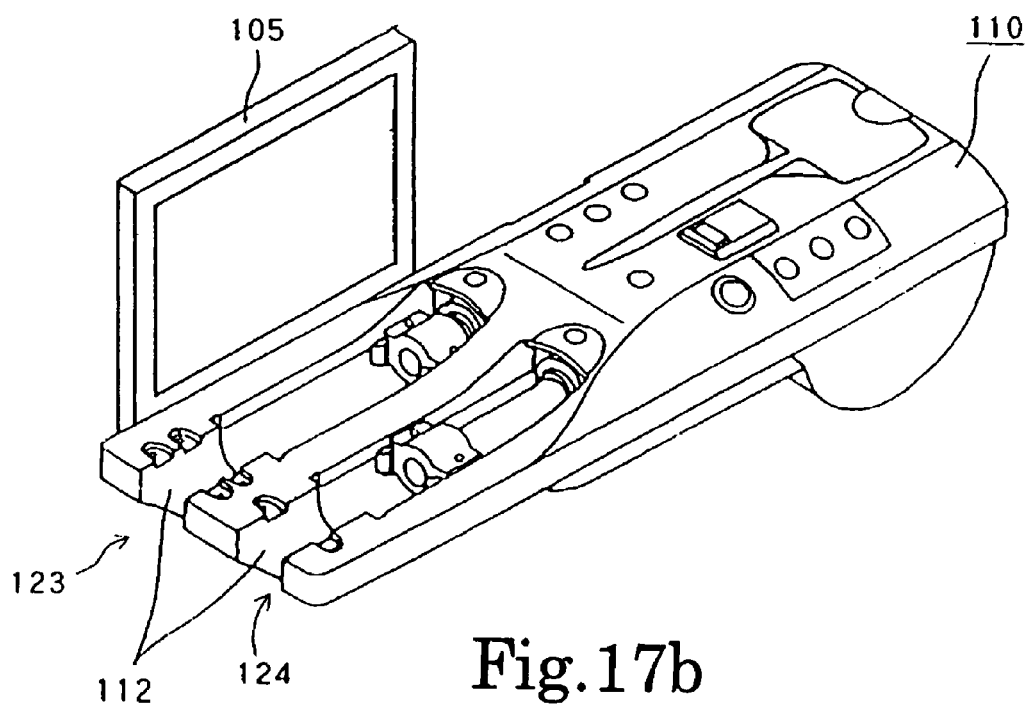

In FIGS. 17a and 17b, since touch panel 105 is positioned adjacent to medium injection mechanism 123 and solution injection mechanism 124, the operator can directly and easily recognize entered injection graphs when the injection graphs for medium injection mechanism 123 and solution injection mechanism 124 are displayed on touch panel 105.

In the above embodiment, it has been assumed for the sake of brevity that a liquid injection rate for a contrast medium, for example, is simply calculated from the speed at which the piston 202 is moved. In reality, liquid syringes 200 are presently commercially available in various sizes, and pistons 202 thereof have various end areas.

The liquid injection rate for a contrast medium or the like depends on both the speed of movement and the end area of piston 202. Consequently, if liquid injector 100 employs liquid syringes 200 of various sizes, then the data of end areas of pistons 202 for the various sizes of liquid syringes 200 may be registered, and when the type of liquid syringe 200 used is entered, the data of the end area of corresponding piston 202 may be read.

To read the data of the end area, it is necessary to enter the types of liquid syringes 200. For example, as disclosed in Japanese patent application No. 2002-021762, when various liquid syringes 200 are set on injection heads 110 using respective dedicated cylinder adapters (not shown), injection head 110 may acquire identification data of liquid syringes 200 and the contrast mediums from the cylinder adapters. Thus, no special input actions to enter the types of liquid syringes 200 are required.

Alternatively, the data of the types of liquid syringes 200 may be encoded on bar codes (not shown) applied to various liquid syringes 200, and may then be read by injection head 110 for allowing liquid injector 100 to identify the types of liquid syringes 200.

In the above embodiment, the injection of liquids with liquid injector 100 and the capture of images with CT scanner 300 are individually manually controlled and carried out. However, liquid injector 100 and CT scanner 300 may communicate with each other for their operations to be interlinked.

For example, when the schematic image of a region to be imaged is entered into liquid injector 100, the data of the region to be imaged may be set in CT scanner 300 in response to the entry of the schematic image into liquid injector 100. In this manner, the burden on the operator to operate liquid injector 100 and CT scanner 300 is lessened.

In the above embodiment, CT scanner 300 is used as an imaging diagnostic apparatus, and liquid injector 100 injects a contrast medium for use therewith into subjects. However, an MIR apparatus or a PET apparatus may be used as an imaging diagnostic apparatus, and liquid injector 100 may inject a contrast medium for use therewith into subjects.

In the above embodiment, CPU 131 operates according to the computer program stored in RAM 133 to logically perform the various functions as the various means of liquid injector 100. However, the above functions may be implemented by pieces of hardware, or some of the functions may be stored as software in RAM 133 and the others implemented by pieces of hardware.

While preferred embodiments of the present invention have been described using specific terms, such description is for illustrative purposes only, and it is to be understood that changes and variations may be made without departing from the spirit or scope of the following claims.

What is claimed is:

1. A liquid injector for injecting at least a liquid into a subject with injection performing means, comprising:
   a touch panel that displays data and accepts input actions;
   image displaying means for displaying a plotting chart image having a vertical axis and a horizontal axis on the touch panel;
   graph entering means for accepting an input action for an operator to enter an injection graph by drawing the injection graph having chronologically changing injecting conditions in a form of a free curve, a plurality of straight lines, a plurality of passing points, or a plurality of rectangular regions directly into the displayed plotting chart image on the touch panel;
   graph storing means for storing data of the entered injection graph;
   graph displaying means for displaying an image of the entered injection graph whose data is stored on said displayed plotting chart image on the touch panel; and
   injection control means for controlling operation of said injection performing means in real-time according to said entered injection graph.

2. A liquid injector according to claim 1, further comprising:
   time measuring means for measuring a time which has elapsed from at least a start of injection of the liquid;
   said image displaying means comprising means for displaying said plotting chart image whose vertical axis represents liquid injection rates and horizontal axis represents liquid injection times;
   said graph entering means comprising means for accepting an input action to enter said injection graph which represents a liquid injection rate at each liquid injection time into said plotting chart image; and said injection control means comprising means for controlling operation of said injection performing means in real-time according to the measured time and said entered injection graph.

3. A liquid injector according to claim 2, further comprising:
quantity calculating means for calculating an injected quantity of the liquid as the area of a chart portion between said injection graph and said horizontal axis; and
quantity displaying means for displaying data of the calculated injected quantity of the liquid.

4. A liquid injector according to claim 3, wherein said graph entering means comprises means for entering said plurality of rectangular regions as said injection graph;
said graph displaying means comprising means for displaying said injection graph as said rectangular regions on said plotting chart image;
said quantity calculating means comprising means for calculating the injected quantity of the liquid as the area of each of said rectangular regions; and
said quantity displaying means comprising means for displaying the calculated injected quantity for each of said rectangular regions.

5. A liquid injector according to claim 1, further comprising:
time measuring means for measuring a time which has elapsed from at least a start of injection of the liquid;
said image displaying means comprising means for displaying said plotting chart image whose vertical axis represents quantities to be injected of the liquid and horizontal axis represents liquid injection times;
said graph entering means comprising means for accepting an input action to enter said injection graph which represents a quantity of the liquid to be injected at each liquid injection time into said plotting chart image; and
said injection control means comprising means for controlling operation of said injection performing means in real-time according to the measured time and said entered injection graph.

6. A liquid injector according to claim 1, further comprising:
quantity detecting means for detecting an injected quantity of the liquid from at least a start of injection of the liquid;
said image displaying means comprising means for displaying said plotting chart image whose vertical axis represents liquid injection rates and horizontal axis represents quantities to be injected of the liquid;
said graph entering means comprising means for accepting an input action to enter said injection graph which represents a liquid injection rate at each quantity of the liquid to be injected into said plotting chart image; and
said injection control means comprising means for controlling operation of said injection performing means in real-time according to the detected injected quantity and said entered injection graph.

7. A liquid injector according to claim 1, wherein said graph entering means comprises means for entering said free curve as said injection graph;
said graph displaying means comprising means for displaying said injection graph as said free curve.

8. A liquid injector according to claim 1, wherein said graph entering means comprises means for entering said plurality of straight lines as said injection graph;
said graph displaying means comprising means for displaying said injection graph as said plurality of straight lines.

9. A liquid injector according to claim 1, wherein said graph entering means comprises means for entering said plurality of straight lines as said injection graph, said liquid injector further comprising:
graph converting means for converting data of the straight lines as said injection graph into data of a free curve;
said graph storing means comprising means for storing data of said injection graph as converted into said free curve;
said graph displaying means comprising means for displaying said injection graph as said free curve; and
said injection control means comprising means for controlling operation of said injection performing means according to said injection graph as said free curve.

10. A liquid injector according to claim 1, wherein said graph entering means comprises means for entering said plurality of passing points as said injection graph, said liquid injector further comprising:
graph converting means for generating data of a plurality of straight lines produced by successively joining said passing points, as said injection graph;
said graph storing means comprising means for storing the generated data of said injection graph;
said graph displaying means comprising means for displaying said injection graph as said successive straight lines; and
said injection control means comprising means for controlling operation of said injection performing means according to said injection graph as said successive straight lines.

11. A liquid injector according to claim 1, wherein said graph entering means comprises means for entering said plurality of passing points as said injection graph, said liquid injector further comprising:
graph converting means for generating data of a free curve successively passing through said passing points, as said injection graph;
said graph storing means comprising means for storing the generated data of said injection graph;
said graph displaying means comprising means for displaying said injection graph as said free curve; and
said injection control means comprising means for controlling operation of said injection performing means according to said injection graph as said free curve.

12. A liquid injector according to claim 11, wherein said graph entering means comprises means for entering input actions to vertically move an upper side of each of said rectangular regions and to horizontally move a right side of each of said rectangular regions.

13. A liquid injector according to claim 1, wherein said graph entering means comprises means for entering said plurality of rectangular regions as said injection graph, and said graph displaying means comprises means for displaying said injection graph as said rectangular regions.

14. A liquid injector according to claim 1, wherein said graph entering means comprises means for entering a period for interrupting the injection of the liquid into the displayed injection graph, and said injection control means comprising means for temporarily inactivating said injection performing means.

15. A liquid injector according to claim 14, further comprising:
situation displaying means for displaying a remaining time of said period for interrupting the injection of the liquid, together with said injection graph, in real-time on said graph displaying means.

16. A liquid injector according to claim 1, further comprising:
    situation displaying means for displaying an injecting situation of said injection performing means, together with said injection graph, in real-time on said graph displaying means.

17. A liquid injector according to claim 1, further comprising:
    an injection head for removably holding a liquid syringe which comprises a cylinder filled with at least said liquid and a piston slidably inserted in said cylinder;
    said injection performing means comprising means for moving said cylinder and said piston relatively to each other while said liquid syringe is being held by said injection head; and
    said touch panel being connected to said injection head parallel thereto.

18. A liquid injector according to claim 1, further comprising:
    image storage means for storing data of schematic images of a plurality of body sections of the human body and schematic images of a plurality of regions to be imaged of the human body in association with each other;
    section display means for displaying the schematic images of the body sections in the shape of a human body;
    section input means for accepting an input action to select one of the displayed schematic images of the body sections;
    region displaying means for displaying the schematic image of at least one of said regions to be imaged in relation to the selected schematic image of the body section; and
    region input means for accepting an input action to select the displayed schematic image of at least one of said regions to be imaged;
    said injection performing means comprising means for injecting at least a contrast medium as said liquid into said subject whose fluoroscopic image is to be captured by an imaging diagnostic apparatus;
    said graph entering means comprising means for entering said injection graph for each of said regions to be imaged of the human body;
    said graph storing means comprising means for storing data of said injection graph for each of said regions to be imaged; and
    said injection control means comprising means for controlling operation of said injection performing means according to the injection graph for the selected region to be imaged.

19. A liquid injector according to claim 1, wherein said injection performing means comprises a medium injection mechanism for injecting a contrast medium as said liquid and a solution injection mechanism for injecting a saline solution as said liquid;
    said graph entering means comprising means for entering injection graphs for said contrast medium and said saline solution which share liquid injection times; and
    said injection control means comprising means for controlling operation of said medium injection mechanism and said solution injection mechanism in an interlinked fashion according to said injection graphs for said contrast medium and said saline solution.

20. A liquid injector accordingly to claim 1, further comprising:
    region displaying means for displaying at least one schematic image of at least one of regions to be imaged of the human body on the touch panel; and
    region input means for accepting an input action to select the displayed schematic image of the region to be imaged;
    said graph entering means comprising means for entering said injection graph for each of the regions to be imaged;
    said graph storing means comprising means for storing data of said injection graph for each of the regions to be imaged; and
    said injection control means comprising means for controlling operation of said injection performing means according to the injection graph for the selected region to be imaged.

21. A liquid injector according to claim 20, further comprising:
    section displaying mans for displaying schematic images of body sections in a shape of a human body on the touch panel;
    section input means for accepting an input action to select one of the displayed schematic images of the body sections; and
    said region displaying means displays the schematic image of the regions to be imaged in relation to the selected schematic image of the body section.

* * * * *